(12) United States Patent
Emerick et al.

(10) Patent No.: US 9,597,203 B2
(45) Date of Patent: Mar. 21, 2017

(54) MODULAR HUMERAL IMPLANT

(71) Applicant: Tornier, Inc., Bloomington, MN (US)

(72) Inventors: Bradley Grant Emerick, Columbia City, IN (US); Brian C. Hodorek, Winona Lake, IN (US); Matthew Victor Kartholl, Fort Wayne, IN (US)

(73) Assignee: Tornier, Inc., Bloomington, MN (US)

( * ) Notice: Subject to any disclaimer, the term of this patent is extended or adjusted under 35 U.S.C. 154(b) by 0 days.

(21) Appl. No.: 14/668,892

(22) Filed: Mar. 25, 2015

(65) Prior Publication Data
US 2016/0278945 A1 Sep. 29, 2016

(51) Int. Cl.
*A61F 2/40* (2006.01)
*A61F 2/46* (2006.01)

(52) U.S. Cl.
CPC .............. *A61F 2/4684* (2013.01); *A61F 2/40* (2013.01); *A61F 2/4014* (2013.01); *A61F 2/4059* (2013.01); *A61F 2002/4011* (2013.01)

(58) Field of Classification Search
CPC .. A61F 2/40; A61F 2/46; A61F 2/4684; A61F 2/4014; A61F 2/4059; A61F 2002/4011; A61F 2/384
USPC ...................... 623/19.11–19.14, 33
See application file for complete search history.

(56) References Cited

U.S. PATENT DOCUMENTS

| | | | | |
|---|---|---|---|---|
| 4,787,907 A * | 11/1988 | Carignan | .................. | A61F 2/28 623/23.44 |
| 5,108,437 A * | 4/1992 | Kenna | .................. | A61F 2/3672 623/16.11 |
| 5,352,227 A * | 10/1994 | O'Hara | .................. | A61B 17/72 606/62 |
| 5,569,263 A * | 10/1996 | Hein | .................. | A61B 17/1659 606/102 |
| 5,860,982 A * | 1/1999 | Ro | .................. | A61F 2/4607 606/102 |
| 5,876,459 A * | 3/1999 | Powell | .................. | A61F 2/3609 623/23.15 |
| 6,197,065 B1 * | 3/2001 | Martin | .................. | A61B 17/164 623/23.17 |

(Continued)

FOREIGN PATENT DOCUMENTS

| | | |
|---|---|---|
| EP | 1314407 | 5/2003 |
| EP | 1681038 A2 | 7/2006 |
| WO | WO 2012/051552 | 4/2012 |

OTHER PUBLICATIONS

International Search and Written Opinion for PCT/US2016/018803 dated Aug. 9, 2016 in 17 pages.

*Primary Examiner* — Alvin Stewart
(74) *Attorney, Agent, or Firm* — Knobbe, Martens, Olson & Bear, LLP

(57) ABSTRACT

Modular humeral implants and methods of use. A humeral implant can include a stem portion, a metaphyseal portion, a locking element, and an intermediate portion. The intermediate portion can include at least one spacer. Each spacer can include a proximal engagement feature, a distal engagement feature, a lumen extending longitudinally through the spacer, and a pin slidable within the lumen of the spacer. Distal movement of a locking element in the metaphyseal portion can translate the pin of each spacer to secure the metaphyseal portion, the intermediate portion, and the stem portion in a locked configuration.

18 Claims, 16 Drawing Sheets

(56) References Cited

U.S. PATENT DOCUMENTS

| | | | |
|---|---|---|---|
| 6,264,699 B1 * | 7/2001 | Noiles | A61F 2/30734 623/20.15 |
| 6,319,286 B1 * | 11/2001 | Fernandez | A61F 2/30734 623/16.11 |
| 6,432,110 B1 * | 8/2002 | Richelsoph | A61F 2/4684 606/62 |
| 6,454,810 B1 * | 9/2002 | Lob | A61B 17/72 606/62 |
| 6,626,951 B1 * | 9/2003 | Gramnas | A61F 2/78 292/306 |
| 7,125,423 B2 * | 10/2006 | Hazebrouck | A61F 2/28 606/62 |
| 7,198,642 B2 * | 4/2007 | Hazebrouck | A61F 2/28 606/62 |
| 7,217,060 B2 * | 5/2007 | Ingimarsson | A61F 2/60 403/105 |
| 7,235,106 B2 * | 6/2007 | Daniels | A61F 2/36 623/22.25 |
| 7,273,499 B2 * | 9/2007 | McCleary | A61B 17/1659 623/18.11 |
| 7,435,263 B2 * | 10/2008 | Barnett | A61F 2/28 623/19.12 |
| 7,998,218 B1 * | 8/2011 | Brown | A61B 17/72 623/20.14 |
| 8,100,982 B2 * | 1/2012 | Heck | A61F 2/28 623/20.35 |
| 8,128,627 B2 * | 3/2012 | Justin | A61B 5/107 606/60 |
| 8,252,002 B2 | 8/2012 | Huff et al. | |
| 8,496,711 B2 * | 7/2013 | Anapliotis | A61F 2/3836 623/16.11 |
| 8,518,122 B2 * | 8/2013 | Anapliotis | A61F 2/36 623/22.42 |
| 9,333,084 B2 * | 5/2016 | Berelsman | A61F 2/3804 |
| 2001/0037154 A1 * | 11/2001 | Martin | A61F 2/3804 623/20.12 |
| 2003/0195636 A1 * | 10/2003 | Coop | A61F 2/78 623/36 |
| 2004/0064187 A1 | 4/2004 | Ball et al. | |
| 2005/0071014 A1 * | 3/2005 | Barnett | A61F 2/28 623/19.14 |
| 2005/0107883 A1 * | 5/2005 | Goodfried | A61F 2/30734 623/20.15 |
| 2009/0306787 A1 * | 12/2009 | Crabtree | A61F 2/4684 623/20.34 |
| 2010/0241239 A1 * | 9/2010 | Smith | A61B 17/1668 623/22.42 |
| 2011/0178604 A1 * | 7/2011 | Porter | A61F 2/30 623/19.14 |
| 2012/0179262 A1 * | 7/2012 | Metcalfe | A61F 2/4014 623/19.14 |
| 2012/0303130 A1 * | 11/2012 | Winslow | A61F 2/4081 623/19.12 |
| 2013/0338780 A1 * | 12/2013 | Berchoux | A61F 2/4003 623/19.11 |
| 2015/0025641 A1 * | 1/2015 | Masson | A61F 2/4014 623/19.13 |

* cited by examiner

MODULAR HUMERAL IMPLANT

BACKGROUND

Field

The present application relates to apparatuses and methods for humeral implants and trial humeral implants.

Description of the Related Art

A typical anatomical shoulder joint replacement attempts to mimic anatomic conditions. For example, a humeral stem and a humeral head replacement are attached to the humerus of the arm and replace the humeral side of the arthritic shoulder joint. The humeral head replacement can articulate with the native glenoid socket or with an opposing glenoid resurfacing device.

For more severe cases, the standard treatment is a reverse reconstruction, which includes reversing the kinematics of the shoulder joint. A reverse shoulder prosthesis can be provided by securing a semi-spherical device (sometimes called a glenosphere) to the glenoid and implanting a humeral stem with a cavity capable of receiving the glenosphere.

Before implanting the humeral implant, it may be desirable to trial the humeral implant to determine an appropriate length of the stem, appropriate inclination angle of the articulating head, and/or size of the articulating head, or other characteristics of the implant. The trial humeral implant can be assembled and then inserted into the humerus. Afterwards, the entire trial implant can be removed, and the definitive humeral implant can be chosen and implanted in the bone.

SUMMARY

Humeral implants utilize modular components that can be assembled utilizing different lengths and diameters of stems, spacers, and metaphases. Some humeral implants are assembled by screwing the components of the implant together and then driving a screw through the entire implant or separately securing each component to an adjacent component.

Utilizing the same components as the definitive humeral implant and supplying all the different sizes of spacers for trialing is expensive and cumbersome, for example, because assembling the components and driving the screw through each trial implant can be difficult. Thus, there is a need for definitive humeral implants and/or trial humeral implants that reduce the number of components, reduce the number of steps for assembly, and/or make assembly easier.

Certain aspects of this disclosure are directed toward a humeral implant, including a metaphyseal portion, an intermediate portion, and a stem portion. The humeral implant can be assembled together by sliding each portion of the implant in a transverse direction relative to a longitudinal axis of an adjacent portion and into engagement with the adjacent portion. For example, the metaphyseal portion can include a slot and the intermediate portion can include a protrusion (or vice versa). The protrusion of the intermediate portion can slide into the slot of the metaphyseal portion by sliding the intermediate portion in a transverse direction relative to the longitudinal axis of the metaphyseal portion. As another example, the intermediate portion can include a slot and the stem portion can include a protrusion (or vice versa). The protrusion of the stem portion can slide into the slot of the intermediate portion by sliding the stem portion in a transverse direction relative to the longitudinal axis of the intermediate portion. This sliding motion can be less cumbersome and faster than screwing the separate components together.

In some configurations, the portions of the humeral implant can be configured to engage each other unilaterally (e.g., a first component can only engage a corresponding second component when the second component is in a single orientation/configuration or when the second component is introduced from a particular side). For example, the metaphyseal portion can be configured to only engage the intermediate portion by introducing the intermediate portion from a particular side of the intermediate portion and moving the intermediate in a direction transverse to a longitudinal axis of the metaphyseal portion. As another example, the intermediate portion can be configured to only engage the stem portion by introducing the stem portion from a particular side of the stem portion and moving the stem portion in a direction transverse to a longitudinal axis of the stem portion. The direction in which the metaphyseal portion engages the intermediate portion may be the same as or different from the direction in which the intermediate portion engages the stem portion. Limiting the orientation of assembly may be desirable to ensure each portion of the implant is properly oriented.

As described above, the intermediate portion can include at least one spacer. Each spacer can include a proximal engagement feature and a distal engagement feature. For configurations with multiple spacers (e.g., two, three, or more), the intermediate portion can be assembled by sliding each spacer in a transverse direction relative to a longitudinal axis of an adjacent spacer and into engagement with the adjacent spacer. For example, the distal engagement feature of a first spacer can be a slot and a proximal engagement feature of a second spacer can be a protrusion (or vice versa). The protrusion of the second spacer can slide into the slot of the first spacer by sliding the second spacer in a transverse direction relative to the longitudinal axis of the first spacer.

In some configurations, the spacers can be configured to engage each other unilaterally. In other words, the first spacer can be configured to only engage the second spacer by introducing the spacer from a particular side of the second spacer and moving the second spacer in a single direction transverse to a longitudinal axis of the first spacer. Limiting the orientation of assembly may be desirable to ensure each spacer is properly oriented.

Certain aspects of the disclosure are directed toward a spacer for use in a medical implant. The spacer can include a body portion having a first engagement feature and a second engagement feature. Each of the first engagement feature and the second engagement feature can be configured to engage other components of the medical implant. A lumen can extend longitudinally through the body portion. A pin can be slidable through the lumen of the body portion. At least a distal portion of the pin can include a smooth outer surface. The pin can include a flange portion configured to limit proximal and/or distal movement of the pin. A spring can be positioned radially between the pin and the body portion.

Certain aspects of this disclosure are directed toward a method of securing the portions of the humeral implant in a locked configuration. To accomplish this, the intermediate portion can include one or more spacers (e.g., one, two, three, or more). Each spacer can include a pin slidable within a lumen of the spacer. After the metaphyseal portion, the intermediate portion, and the stem portion have been assembled (as described above or otherwise), distal movement of a locking element in the metaphyseal portion can translate the pin of each spacer to secure the humeral implant in a locked configuration. This method of securement decreases the total time necessary to secure the humeral implant together by not requiring a user to drive a screw through a substantial length of the humeral implant or separately secure adjacent portions of the implant.

Any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No individual aspects of this disclosure are essential or indispensable.

BRIEF DESCRIPTION OF THE DRAWINGS

Various embodiments are depicted in the accompanying drawings for illustrative purposes, and should in no way be interpreted as limiting the scope of the embodiments. Furthermore, various features of different disclosed embodiments can be combined to form additional embodiments, which are part of this disclosure.

DETAILED DESCRIPTION

Humeral implants can be monolithic structures or include modular components. In either case, it may be desirable to create a temporary/trial implant to help determine the appropriate dimensions for a permanent implant. For example, the trial implant can include an articular body, a metaphyseal portion, one or more spacers, and/or a stem portion. The stem portion provides a platform for the metaphyseal portion, which can be adapted to receive an anatomic or a reversed articular body. The spacers can be utilized to adjust a length of the implant.

Humeral Implants

Figure 1:
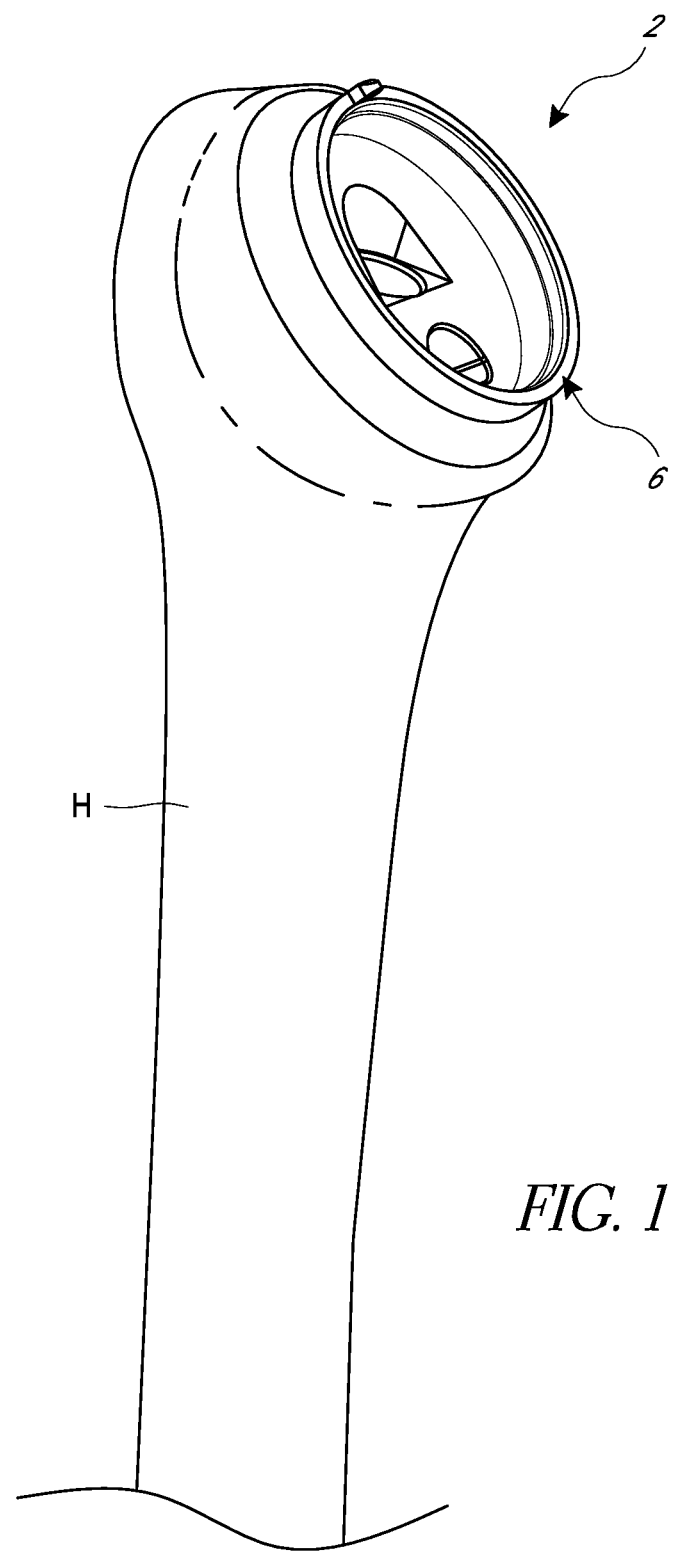
FIG. 1 illustrates a humeral implant implanted in a humerus.

FIG. 1 illustrates a humeral implant 2, and more specifically, a reverse humeral implant implanted/positioned in a humerus H. A reversed metaphyseal portion 6 of the implant 2 is positioned within the humerus and can be configured to receive an articular component configured to interface with an opposing glenoid component. Although, depending on the needs of the patient, the humeral implant 2 may include an anatomic metaphyseal portion (see FIGS. 8A and 8B).

Figure 2A:
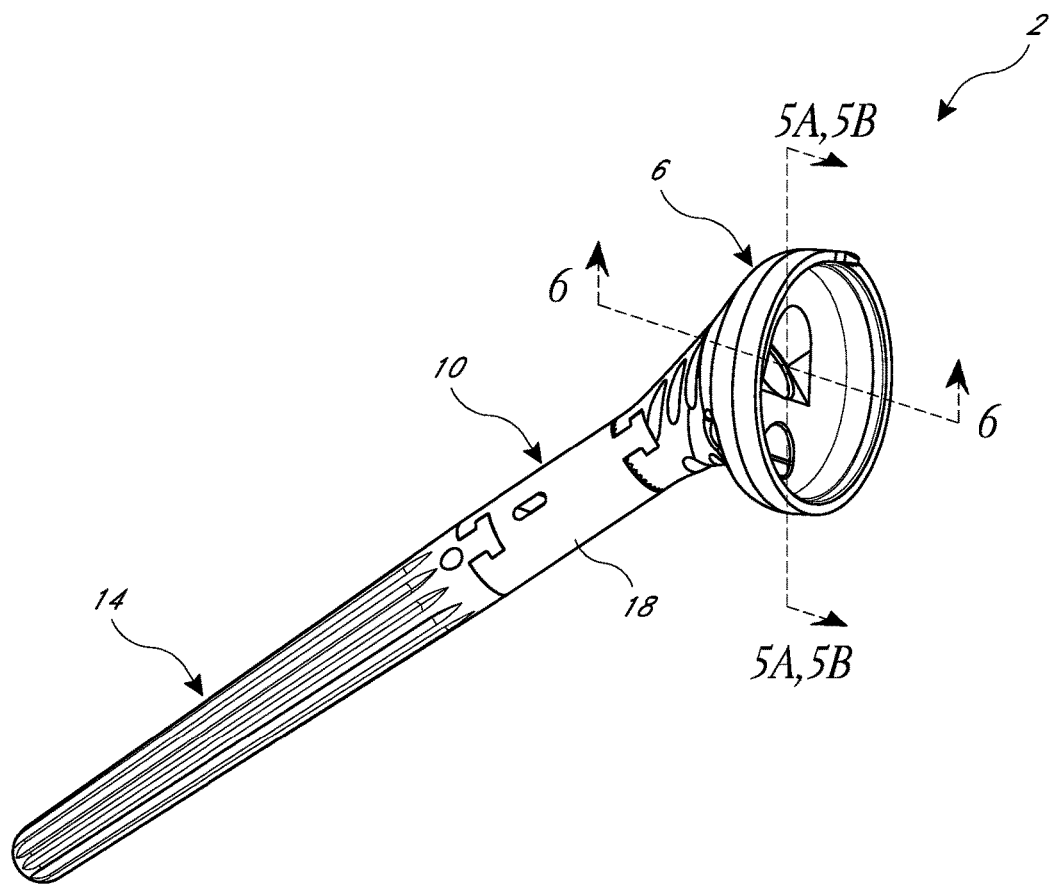
FIG. 2A illustrates a perspective view of an embodiment of a humeral implant including a single spacer.

FIG. 2A illustrates the humeral implant 2 including the metaphyseal portion 6, an intermediate portion 10, and a stem portion 14. As illustrated, the intermediate portion is positioned between the metaphyseal portion 6 and the stem portion 14. Depending on the desired length of the implant 2, the intermediate portion 10 can include one or more spacers 18 (e.g., one, two, three, or more). In one non-limiting example, a shorter length implant 2 may utilize one spacer 18 (see FIG. 2A), whereas a longer length implant (see FIG. 2B) may utilize two or more spacers 18. When implanted, the intermediate portion 10 and the stem portion 14 can be inserted into the humerus H and at least a portion of the metaphyseal portion 6 can remain exterior to a resected portion of the humerus H (see FIG. 1).

Figure 3:
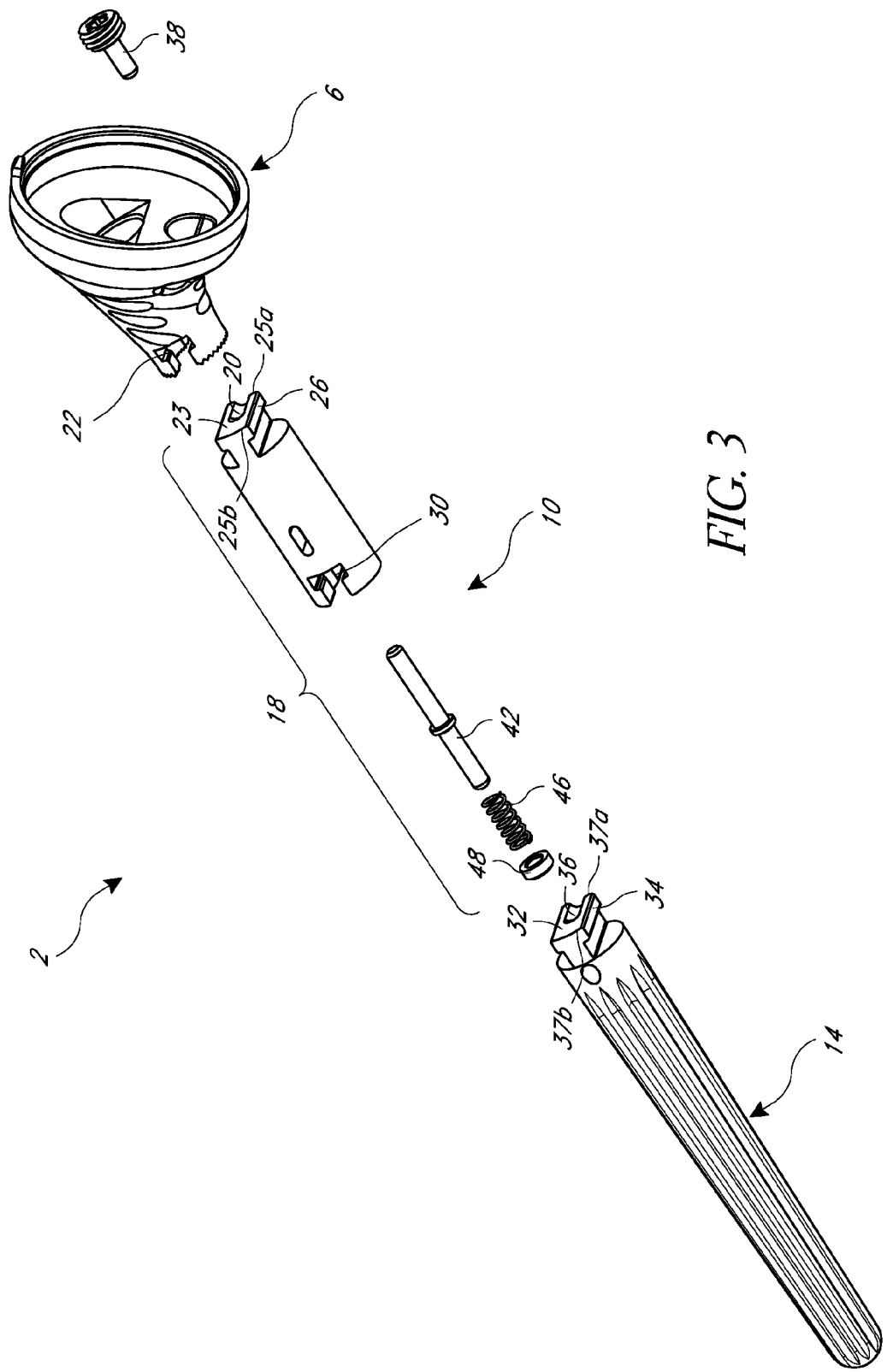
FIG. 3 illustrates an exploded view of the humeral implant shown in FIG. 2A.

As shown in FIG. 3, the metaphyseal portion 6 can include a metaphyseal engagement feature 22. The metaphyseal engagement feature 22 can be configured to engage a proximal engagement feature 26 of the spacer 18. For example, as shown in FIG. 3, the metaphyseal engagement feature 22 can be a slot, and the proximal engagement feature 26 of the spacer 18 can be a protrusion. Although in other examples, the metaphyseal engagement feature 22 can be a protrusion, and the proximal engagement feature 26 of the spacer 18 can be a slot. More generally, one of the metaphyseal engagement feature 22 and the proximal engagement feature 26 of the spacer 18 can be a slot, and the other of the metaphyseal engagement feature 22 and the proximal engagement feature 26 of the spacer 18 can be a protrusion. Use of slots or similar structures (e.g., recesses, channels, or otherwise) can eliminate rotation between adjacent components when assembled together.

A distal engagement feature 30 of the spacer 18 can be configured to engage a stem engagement feature 34 of the stem portion 14. Additionally, the distal engagement feature 30 can be configured to engage a proximal engagement feature 26 of another spacer (see FIG. 2B and later description). For example, one of the stem engagement feature 34 and the distal engagement feature 30 of the spacer 18 can be a slot, and the other of the stem engagement feature 34 and the distal engagement feature 30 of the spacer 18 can be a protrusion. As shown in FIG. 3, the stem engagement feature 34 can be a protrusion, and the distal engagement feature 30 of the spacer 18 can be a slot. Although in other examples, the stem engagement feature 34 can be a slot, and the distal engagement feature 30 of the spacer 18 can be a protrusion.

As shown in FIG. 3, the engagement features can be T-shaped slots or T-shaped protrusions. More particularly, the T-shaped protrusion is shaped to be slidably received by the T-shaped slot. However, in other embodiments, the protrusions and slots may be dovetailed, spherical, triangular, or otherwise shaped to facilitate engagement in a transverse direction. The shapes of the engagement features need not be the same along a length of the implant 2, however the engagement features are provided complementary in shape. For example, the metaphyseal engagement feature 22 and the proximal engagement feature 26 can be T-shaped, while the distal engagement feature 30 and the stem engagement feature 34 can be rounded. As will be later described, the slots can be structured to only receive the protrusions when the protrusions are introduced from a particular side of the protrusions.

Figure 4:
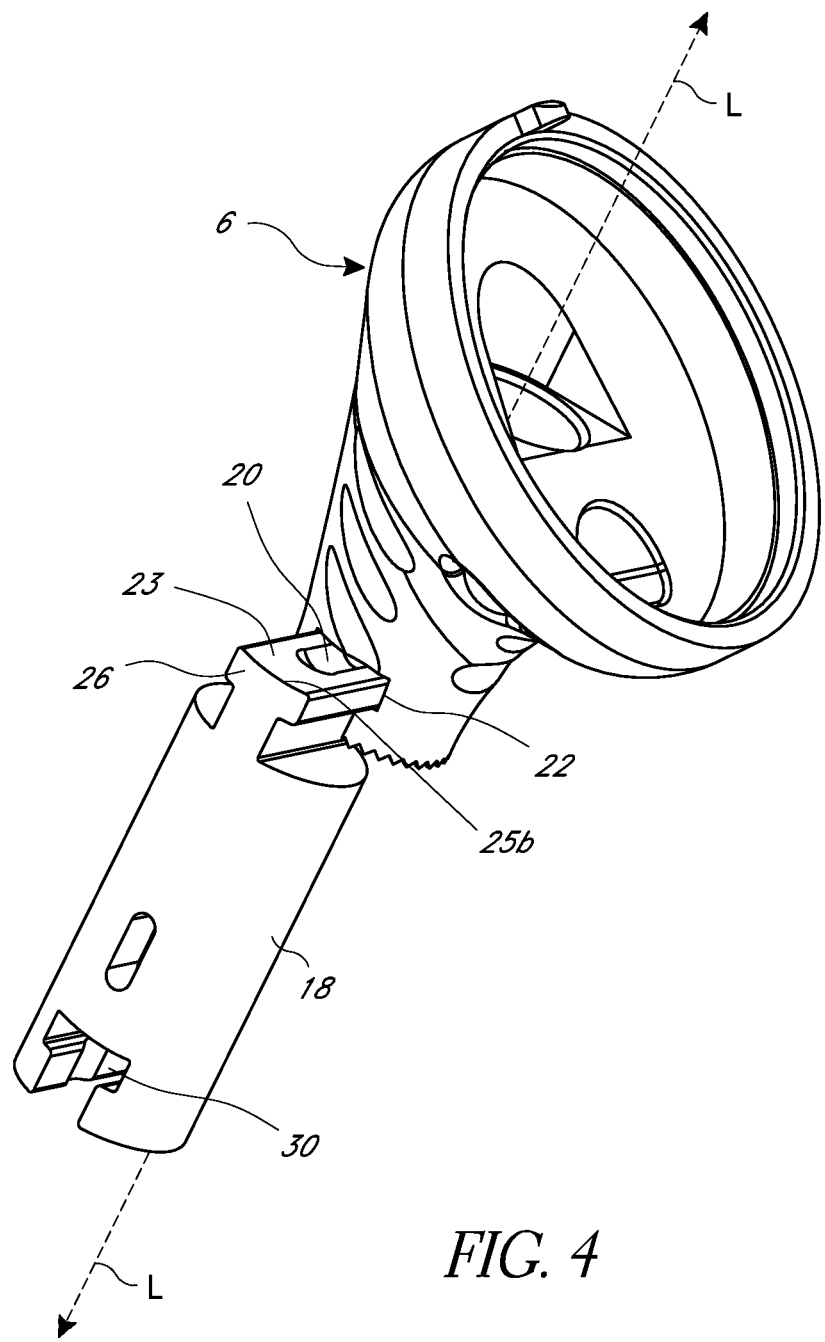
FIG. 4 illustrates a perspective view of an embodiment of a reversed metaphyseal portion partially engaged with a spacer.

The engagement features of each of the metaphyseal portion 6, the intermediate portion 10, and the stem portion 14 of the humeral implant 2 can be shaped such that adjacent portions can be assembled by moving (e.g., translating or sliding) one portion in a transverse direction relative to a longitudinal axis of the adjacent portion. For example, as shown in FIG. 4, the metaphyseal engagement feature 22 can be shaped to engage the proximal engagement feature 26 of the spacer 18 by sliding the spacer 18 in a transverse direction relative to a longitudinal axis L of the metaphyseal portion 6. Although not shown, the distal engagement feature 30 of the spacer 18 can be shaped to engage the stem engagement feature 34 by sliding the stem portion 14 in a transverse direction relative to a longitudinal axis "L" of the spacer 18. This sliding motion can be performed in a single motion.

The metaphyseal portion 6, the intermediate portion 10, and the stem portion 14 of the humeral implant 2 can be configured to engage each other unilaterally (e.g., a first component can only engage a corresponding second component when the second component is in a single orientation/configuration or when the second component is introduced from a particular side). Limiting the direction in which the components can be assembled may be desirable to ensure each component of the implant 2 is properly oriented. For example, the metaphyseal engagement feature 22 can be configured to only engage the proximal engagement feature 26 of the spacer 18 by introducing the proximal engagement feature 26 into the metaphyseal engagement feature 22 from a particular side of the proximal engagement feature 26, e.g., from the side of the proximal engagement feature 26 including the groove 20 (as described further below). The spacer 18 can be moved in a single direction transverse to a longitudinal axis of the metaphyseal portion 6 to fully engage the metaphyseal portion 6 and the spacer 18. To disengage the spacer 18 from the metaphyseal portion 6, the spacer 18 must be retracted in a direction that is opposite from the direction in which the spacer 18 was introduced. Although, other structures can be imagined in which the spacer 18 can be disengaged from the metaphyseal portion 6 by continuing to move the spacer 18 in a direction that is the same as the direction in which the spacer 18 was introduced.

As another example, the distal engagement feature 30 of the spacer 18 can be configured to only engage the stem engagement feature 34 by introducing the stem engagement feature 34 into the distal engagement feature 30 from a particular side of the stem engagement feature 34, e.g., from the side of the stem engagement feature 34 including the groove 36. The stem portion 14 can be moved in a single direction transverse to a longitudinal axis of the stem portion 14. To disengage the stem portion 14 from the spacer 18, the stem portion 14 must be retracted in a direction that is opposite the direction in which the stem portion 14 was introduced. Although, other structures can be imagined in which the stem portion 14 can be disengaged from the spacer 18 by continuing to move the stem portion 14 in a direction that is the same as the direction in which the stem portion 14 was introduced.

As shown in FIG. 4, the proximal engagement feature 26 of the spacer 18 can include a groove 20 (or notch, recess, channel, or otherwise) extending partially across a proximal face 23 of the proximal engagement feature 26. The groove 20 can extend from a first lateral edge 25a of the proximal face 23 (see FIG. 3) to the lumen 56 (not shown). The groove 20 can facilitate proper orientation between the spacer 18 and the metaphyseal portion 6.

Figure 5A:
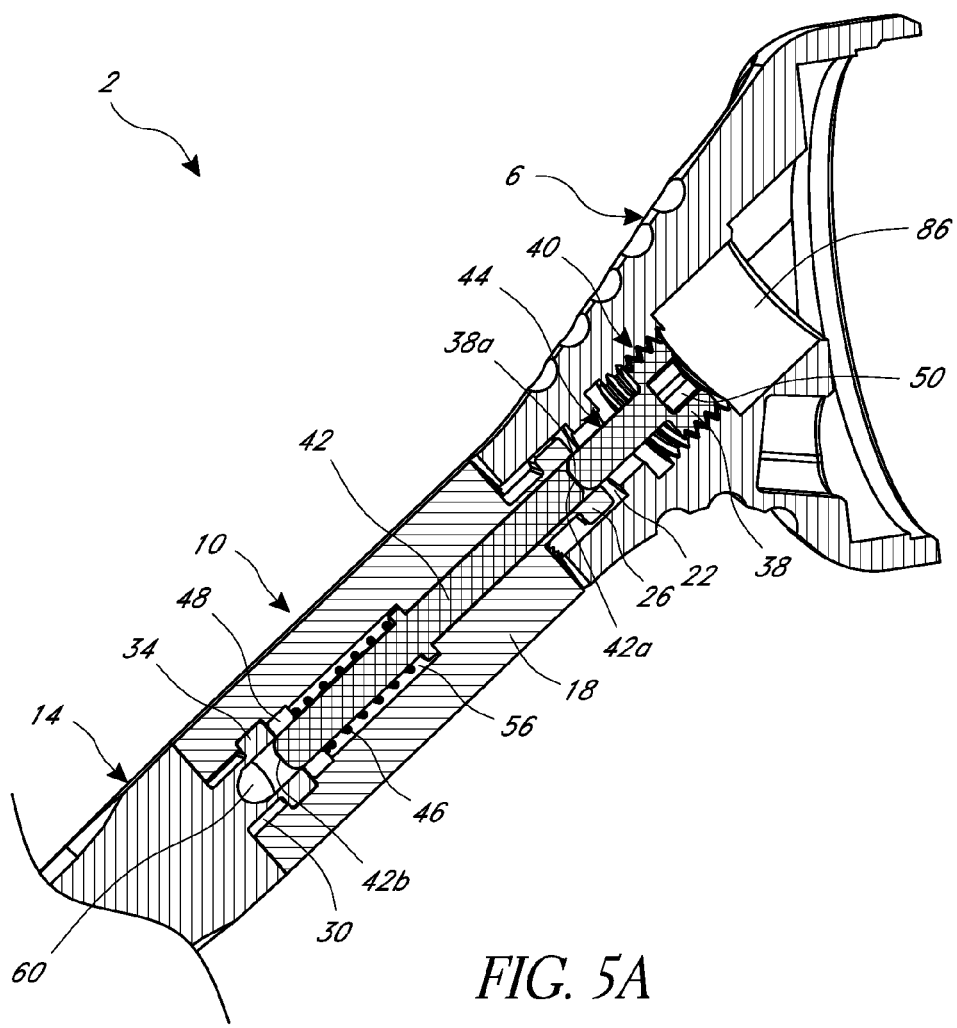
FIG. 5A illustrates a partial cross-section of the humeral implant shown in FIG. 2A taken through line 5A,5B-5A,5B with the humeral implant in an unlocked configuration.

As shown in FIG. 5A, at rest, a distal end 38a of the locking element 38 can extend into the metaphyseal engagement feature 22. The distal end 38a of the locking element 38 can prevent the proximal engagement feature 26 from engaging the metaphyseal engagement feature 22 unless the proximal engagement feature 26 is introduced from the first lateral edge 25a having the groove 20 (see FIG. 4). The groove 20 can be configured to guide the distal end 38a of the locking element 38 toward the lumen 56 (not shown). If the proximal engagement feature 26 is introduced into metaphyseal engagement feature 22 from the opposite second lateral edge 25b of the proximal engagement feature 26 (see FIGS. 3 and 4), the proximal engagement feature 26 will not be able to engage the metaphyseal engagement feature 22.

Similarly, as shown in FIG. 3, the stem engagement feature 34 can include a groove 36 or notch, recess, channel, or otherwise) extending partially across a proximal face 32 of the stem engagement feature 34. The groove 36 can extend from a first lateral edge 37a of the proximal face 32 (see FIG. 3) to the lumen 60 (not shown).

A shown in FIG. 5A, at rest, a distal end 42b of the pin 42 can extend into the stem engagement feature 34. The distal end 42b of the pin 42 can prevent the distal engagement feature 30 from engaging the stem engagement feature 34 unless stem engagement feature 34 is introduced from the first lateral edge 37a having the groove 36. If the stem engagement feature 34 is introduced into the distal engagement feature 30 from the opposite second lateral edge 37b of the stem engagement feature 34 (see FIG. 3), the stem engagement feature 34 will not be able to engage the distal engagement feature 30.

Figure 5B:
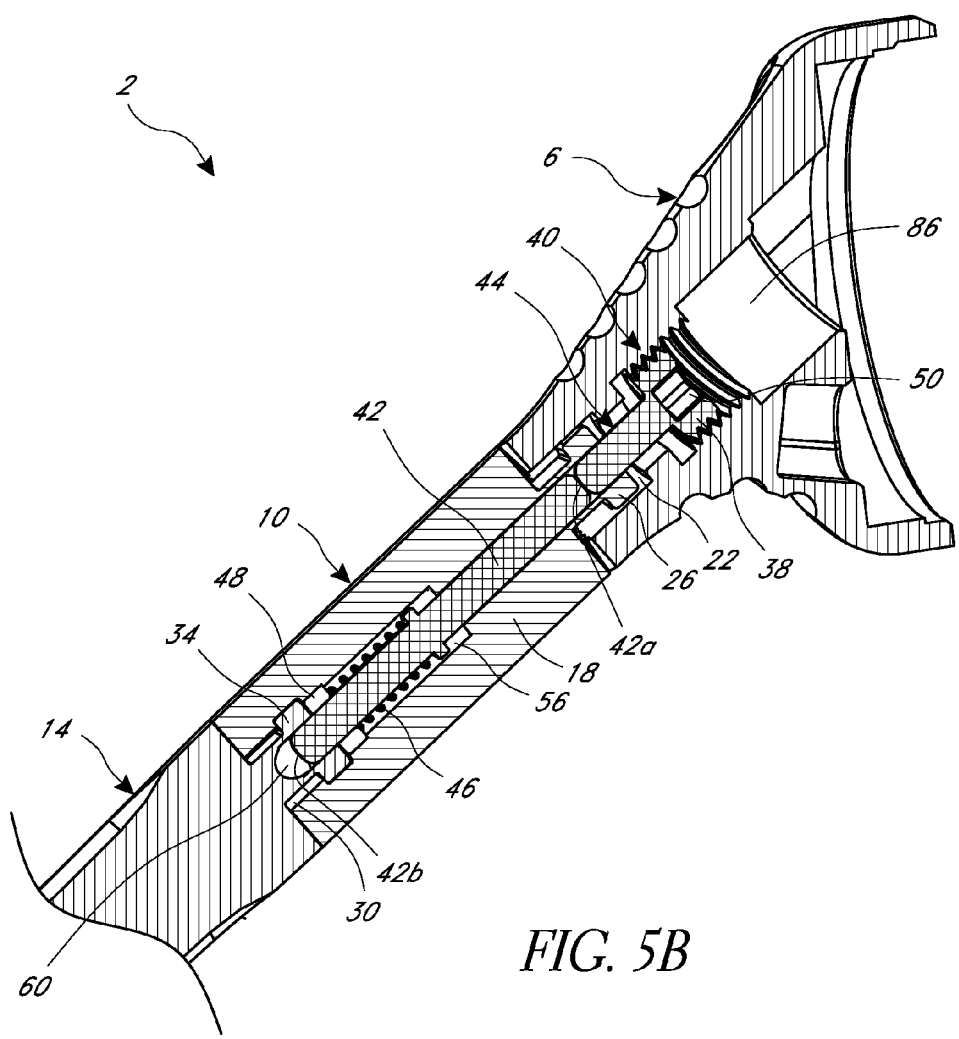
FIG. 5B illustrates a partial cross-section of the humeral implant shown in FIG. 2A taken through line 5A,5B-5A,5B with the humeral implant in a locked configuration.

After the metaphyseal portion 6, the intermediate portion 10, and the stem portion 14 have been assembled (as described above or otherwise), the humeral implant 2 can include a locking assembly to transition the implant 2 from an unlocked configuration (see FIG. 5A) and a locked configuration (see FIG. 5B). In the locked configuration, the metaphyseal portion 6, the intermediate portion 10, and the stem portion 14 can be longitudinally and transversely locked relative to each other.

When the implant 2 is assembled, a lumen 86 of the metaphyseal portion 6 can be longitudinally aligned with a lumen 56 of the spacer 18 and the recess 60 of the stem portion 14 (see FIGS. 5A and 5B). Since the lumens 56, 86 are aligned, a locking element 38 in the metaphyseal portion 6 can be longitudinally aligned with a pin 42 in the spacer 18. The locking element 38 can be sufficiently long to contact a proximal end 42a of pin 42, so the locking element 38 and the pin 42 can form a continuous rod extending through the implant 2. When the implant 2 is assembled, the locking element 38 only partially extends through the adjacent spacer 18. As shown in FIG. 5B, in the locked configuration, a distal end 38a of the locking element 38 may be positioned in a portion of the lumen 56 extending through the proximal engagement feature 26 of the spacer 18.

Distal movement of the locking element 38 (e.g., by pushing, rotating, or otherwise moving) can translate the pin 42 longitudinally to secure the humeral implant 2 in a locked configuration (see FIG. 5B). In the locked configuration, at least a distal portion of the locking element 38 can extend into a lumen 56 of the spacer 18 such that the locking element 38 traverses the intermediate portion 10 and the metaphyseal portion 6. At least a distal portion of the pin 42 can be positioned in a recess 60 of the stem portion 6 such that the pin 42 traverses the intermediate portion 10 and the stem portion 6.

As shown in FIGS. 5A and 5B, the locking element 38 can include a proximal portion 40 and a distal portion 44. The proximal portion 40 of the locking element 38 can threadably engage the metaphyseal portion 6. The distal portion 44 of the locking element can have a smooth exterior surface. Although in other embodiments, the distal portion 44 can be threaded and the proximal portion 40 can be smooth, the locking element 38 can be threaded along an entire length of the locking element 38, or the locking element 38 can be smooth along an entire length of the locking element.

The locking element 38 can include a recess 50 in at least the proximal portion 40 of the locking element 38. The recess 50 can be configured to receive a tool (e.g., screw driver, hex-shaped tool, or otherwise) that can rotate or rotatably engage the locking element 38. Rotation of the locking element 38 can translate the locking element 38 distally (see FIG. 5B) and proximally (see FIG. 5A). In some configurations, less than about four rotations of the locking element (e.g., less than about three, less than about two, or otherwise) can move the implant 2 between the locked configuration and the unlocked configuration. In some configurations, a single rotation (e.g., 360 degrees) of the locking element 38 can move the implant 2 between the locked configuration and the unlocked configuration. A fewer number of rotations may be beneficial to decrease the amount of work and time necessary to assemble and disassemble the implant 2.

To unlock the implant 2, the locking element 38 can be moved proximally (e.g., by pushing, rotating, or otherwise moving) to permit the pin 42 to translate proximally and release the implant 2 from the locked configuration to the unlocked configuration (see FIG. 5A). This method of securement and unsecurement decreases the total time necessary to secure the humeral implant together by not requiring a user to drive a screw through a substantial length of the humeral implant or separately secure adjacent portions of the implant.

Figure 6:
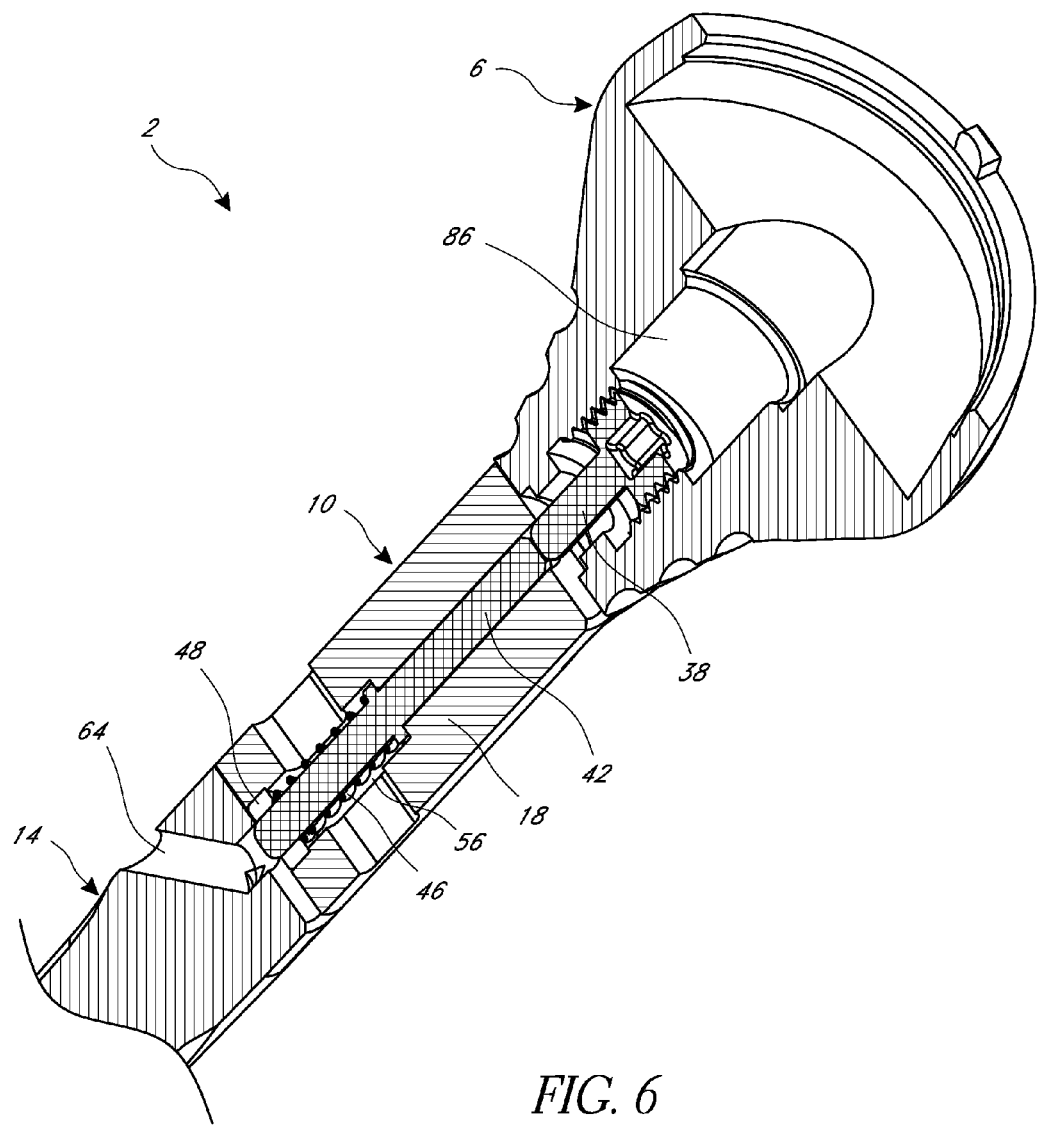
FIG. 6 illustrates a partial cross-section of the humeral implant shown in FIG. 2A taken through line 6-6 with the humeral implant in a locked configuration.

To facilitate release of the implant 2 from the locked configuration, the stem portion 6 can include a channel 64 extending from an outer surface of the stem portion 14 to a distal end of the recess 60 (see FIG. 6). The channel 64 can be shaped to receive an elongate structure (e.g., a pin, guidewire, screw driver, or otherwise) (not shown). The elongate structure can push a distal end of the pin 42 proximally to release the implant from the locked configuration.

To disassemble the implant 2, each component must be retracted in a direction opposite from the direction in which that component was introduced. Since the groove 20 only extends partially across a proximal face 23 of the proximal engagement feature 26, the distal end 38a of the locking element 38 is prevented from moving beyond the lumen 26 and toward the second lateral edge 25b of the proximal engagement feature 26. Similarly, since the groove 36 only extends partially across a proximal face 32 of the stem engagement feature 34, the distal end 42b of the pin 42 is prevented from moving beyond the lumen 60 and toward the second lateral edge 37b of the stem engagement feature 34.

Figure 7A:
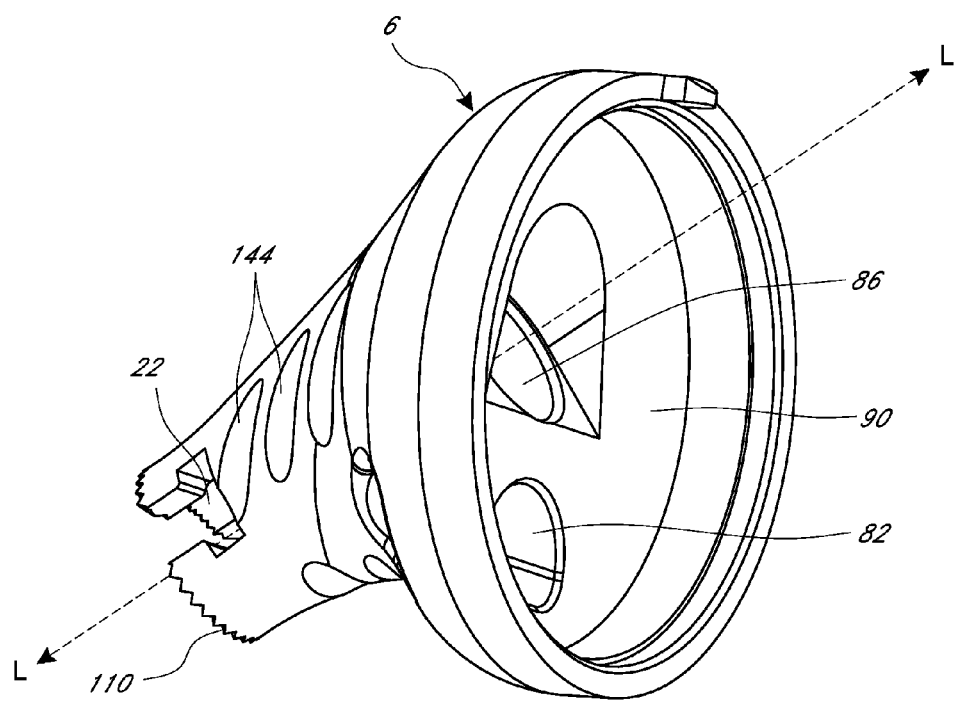
FIG. 7A illustrates a perspective view of a reversed metaphyseal portion.
Figure 7B:
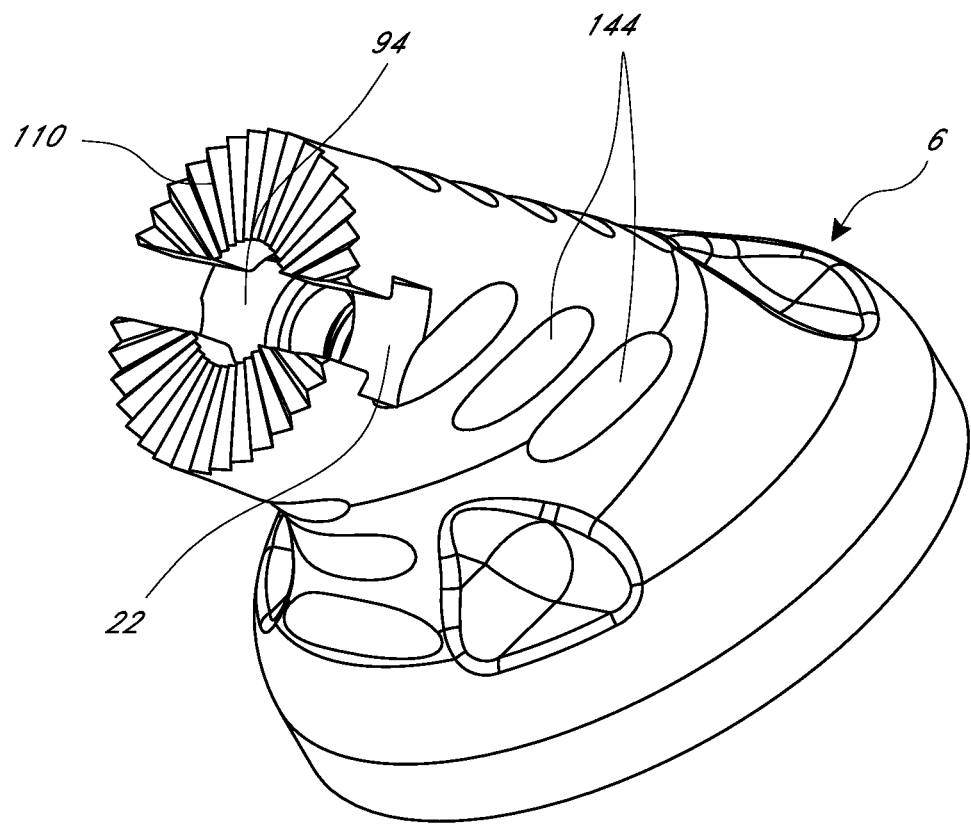
FIG. 7B illustrates an alternate perspective view of the reversed metaphyseal portion shown in FIG. 7A.
Figure 7C:
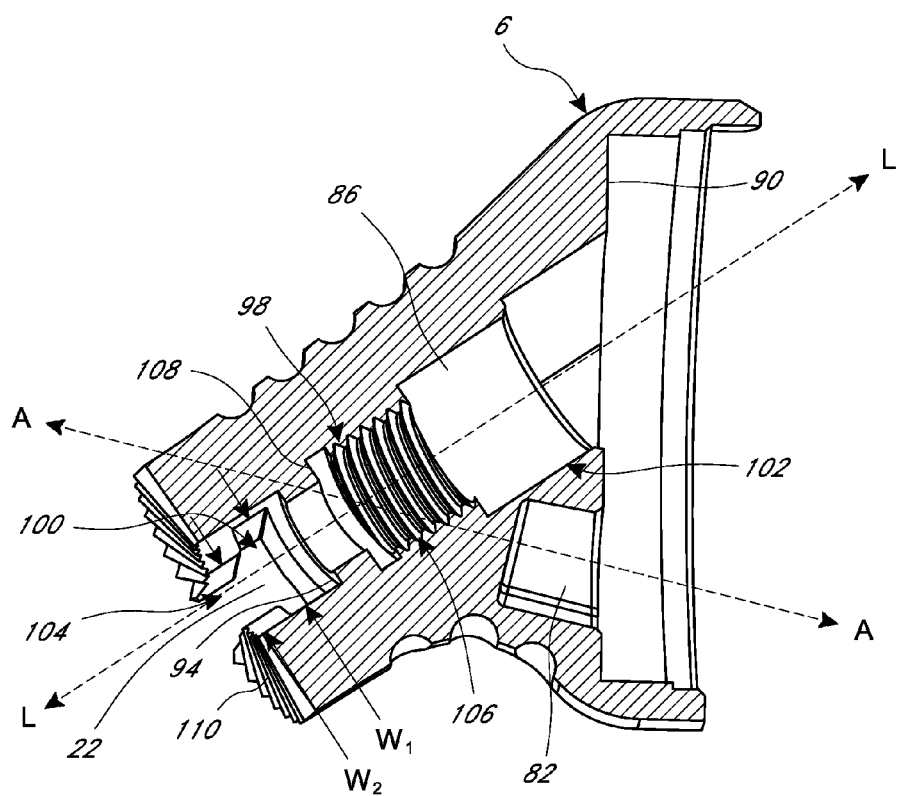
FIG. 7C illustrates a cross-section of the reversed metaphyseal portion shown in FIG. 7A.

Turning to FIGS. 7A-7C, the metaphyseal portion 6 can be a reversed metaphyseal portion. The metaphyseal portion 6 can be configured to receive an articular component having a cavity configured to interface with a glenosphere. An exterior surface of the metaphyseal portion 6 can include a number of scalloped features 144 configured to interface with the bone. A proximal-facing surface 90 can be at an incline relative to a longitudinal axis L of the metaphyseal portion 6 (see FIG. 7A). A distal surface 110 of the metaphyseal portion 6 can include teeth (see FIG. 7B), which can interface with a proximal face of the spacer 18 even if the spacer 18 does not have the corresponding proximal engagement feature 22. If a humeral stem of a previously implanted humeral implant is left in the bone, a metaphyseal portion 6 can interface with the humeral stem using the teeth on the distal surface 110 of the metaphyseal portion 6, even if the humeral stem does not have the T-shaped or otherwise appropriately shaped engagement feature.

As shown in FIG. 7C, the metaphyseal portion 6 can include a first lumen 82 and a second lumen 86. The first lumen 82 can be configured to receive a corresponding engagement feature of the articular component. The first lumen 82 can extend at least partially through the metaphyseal portion 6. The first lumen 82 can extend from a proximal opening at the proximal-facing surface 90 of the metaphyseal portion 6 and extend toward the longitudinal axis L of the metaphyseal portion 6. An axis A extending through first lumen 82 can be positioned at a non-zero angle relative to the longitudinal axis L of the metaphyseal portion 6.

The second lumen 86 can extend entirely through the metaphyseal portion 6 and along a longitudinal axis L of the metaphyseal portion 6 (see FIG. 7C). The second lumen 86 can include a proximal opening and a distal opening. The proximal opening can be positioned at an angle relative to the proximal-facing surface 90 and/or at least partially recessed from the proximal-facing surface 90. The distal opening can be positioned at a distal-facing surface 94 of the metaphyseal portion 6.

The second lumen 86 can include a first portion 98 and a second portion 102 proximal to the first portion 98 (see FIG. 7C). A diameter of the second portion 102 can be greater than a diameter of the first portion 98. The first portion 98 can be configured to receive the locking element 38 (see FIGS. 5A and 5B). At least a section of the first portion 98 can be threaded to threadably engage the locking element 38. For example, a proximal section 106 of the first portion 98 can be configured to receive a threaded portion of the locking element 38. The second lumen 86 can include a shoulder 108 on which the locking element 38 can sit when the implant 2 is in the locked configuration (see FIG. 7C). In other configurations, the entire first portion 98 can be threaded, a distal section of the first portion 98 can be threaded, or the entire first portion 98 can be smooth.

As shown in FIG. 7C, the metaphyseal engagement feature 22 can be a T-shaped slot. The T-shaped slot can include a first portion 100 and a second portion 104. A width $w_1$ of the first portion 100 can be greater than a width $w_2$ of the second portion 104. The second portion 104 can be positioned at an end of the metaphyseal engagement feature 22.

Figure 8A:
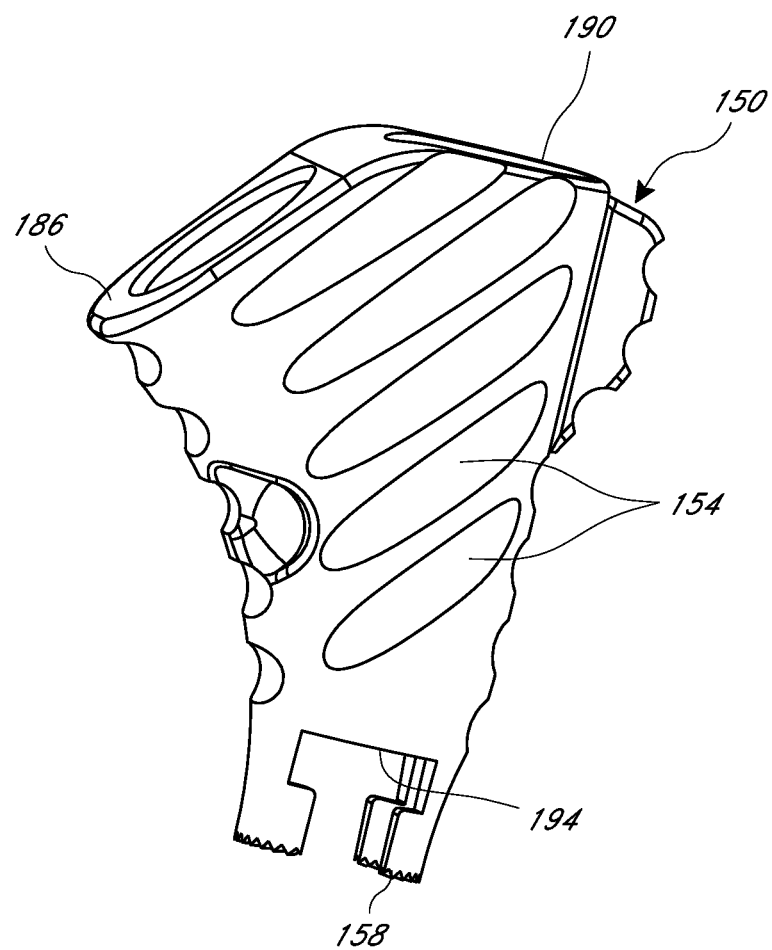
FIG. 8A illustrates a perspective view of an anatomic metaphyseal portion.
Figure 8B:
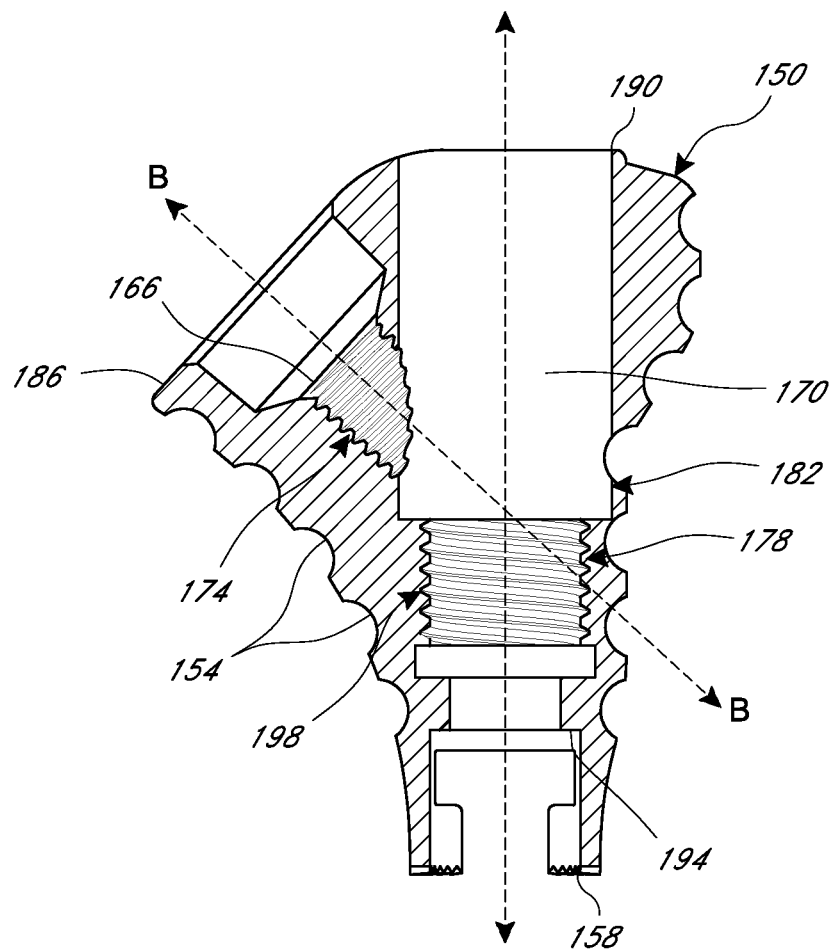
FIG. 8B illustrates a cross-section of the anatomic metaphyseal portion shown in FIG. 8A.

FIGS. 8A and 8B illustrate an anatomic metaphyseal portion 150 that can be used during anatomic shoulder replacements. The anatomic metaphyseal portion 150 can interface with the intermediate portion 10 and the stem portion 14 similar to the reverse metaphyseal portion 6.

Similar to the reverse metaphyseal portion 6, the anatomic metaphyseal portion 150 can include scalloped features 154 on an exterior surface of the metaphyseal portion 150 and/or teeth on a distal surface 158 of the metaphyseal portion 150. The metaphyseal portion 150 can include a metaphyseal engagement feature 156 that can engage the proximal engagement feature 22 of the spacer 18.

The metaphyseal portion 150 can include a first lumen 166 and a second lumen 170 (see FIG. 8B). The first lumen 166 can extend at least partially through the metaphyseal portion 150. The first lumen 166 can extend from a proximal opening at a proximal, inclined surface 186 of the metaphyseal portion 150 and extend toward the longitudinal axis L of the metaphyseal portion 150. The first lumen 166 can include a distal opening along the second lumen 170. An axis B extending through first lumen 166 can be positioned at a non-zero angle relative to the longitudinal axis L of the metaphyseal portion 150. A section 174 of the first lumen 166 can be threaded to threadably engage the articular component.

The second lumen 170 can extend entirely through the metaphyseal portion 150 and along a longitudinal axis L of the metaphyseal portion 150 (see FIG. 8B). The second lumen 170 can include a proximal opening and a distal opening. The proximal opening can be positioned at a proximal-facing surface 190 of the metaphyseal portion 150. The distal opening can be positioned at a distal-facing surface 194 of the metaphyseal portion 150.

The second lumen 170 can include a first portion 178 and a second portion 182 proximal to the first portion 178. A diameter of the second portion 182 can be greater than a diameter of the first portion 178. The first portion 178 can be configured to receive the locking element 38 (see FIGS. 5A and 5B). At least a section of the first portion 178 can be threaded to threadably engage the locking element 38. For example, the proximal section 198 of the first portion 178 can be configured to receive a threaded portion of the locking element 38 (see FIGS. 5A and 5B). In other configurations, the entire first portion 178 can be threaded, a distal section of the first portion 178 can be threaded, or the entire first portion 178 can be smooth.

Figure 9B:
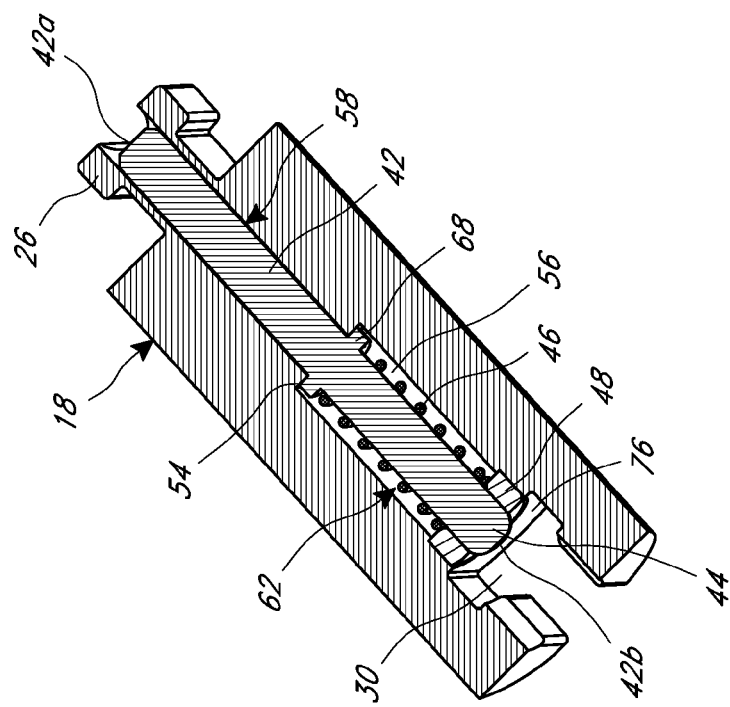
FIG. 9B illustrates a cross-section of the spacer shown in FIG. 9A.
Figure 9A:
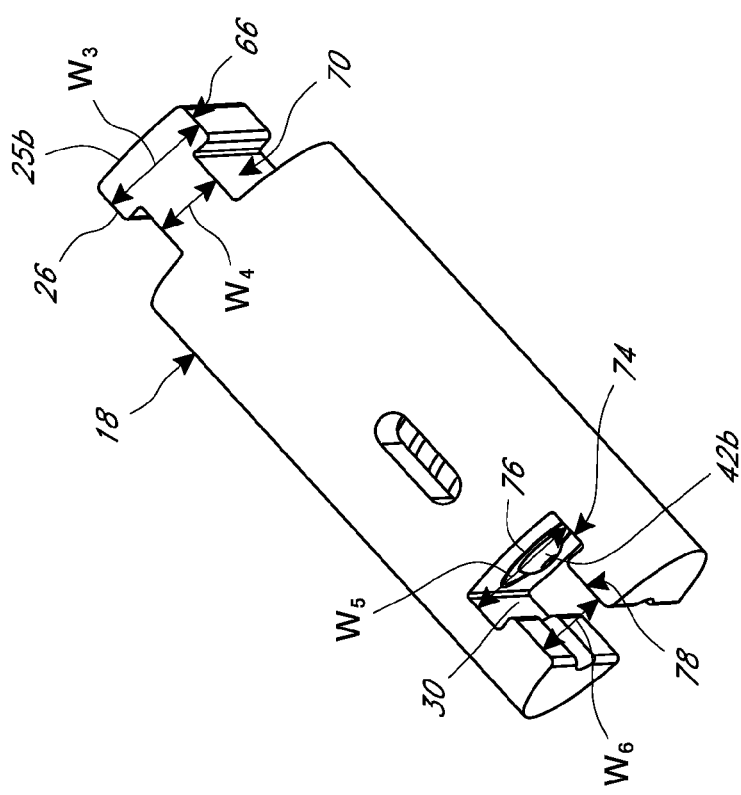
FIG. 9A illustrates a perspective view of a spacer.

FIGS. 9A and 9B illustrate the spacer 18. As described above, the proximal engagement feature 26 can be a T-shaped protrusion. The T-shaped protrusion can include a first portion 66 and a second portion 70. A width $w_3$ of the first portion 66 can be greater than a width $w_4$ of the second portion 70. The first portion 66 can form an end of the spacer 18. The distal engagement feature 30 can be a T-shaped slot. The T-shaped slot can include a first portion 74 and a second portion 78. A width $w_5$ of the first portion 74 can be greater than a width $w_6$ of the second portion 78. The second portion 78 can be positioned at an end of the spacer 18. In other embodiments, the proximal engagement feature 26 can be a slot and the distal engagement feature 30 can be a protrusion.

As shown in FIG. 9B, the body portion 52 can include an interior surface forming the lumen 56. The lumen 56 can include a proximal portion 58 and a distal portion 62. A diameter of the proximal portion 58 can be less than a diameter of the distal portion 62. The junction between the proximal portion 58 and the distal portion 62 can form a shoulder 54. The shoulder 54 can limit proximal movement of the pin 42. For example, the pin 42 can include a flange portion 68. A diameter of the flange portion 68 can be greater than the diameter of the proximal portion 58 such that movement of the pin 42 is limited.

The pin 42 can be slidable within the lumen 56 of the spacer 18. As shown in FIG. 9B, the pin 42 can be smooth along an entire surface of the pin 42. However, in other configurations, a portion of the pin 42 may be threaded to facilitate engagement.

A length of the pin 42 can be less than a length of the body portion 52. At rest, the pin 42 can be sufficiently long such that a proximal end 42a of the pin 42 is positioned in the proximal engagement feature 26 and a distal end 42b of the pin 42 protrudes beyond a distal-facing surface 76 of the spacer 18 (see FIGS. 9A and 9B). In the locked configuration, the pin 42 can be sufficiently long such that the proximal end of the pin 42 is positioned in the proximal engagement feature 26 and a distal end of the pin 42 can be positioned in the stem engagement feature 34 or a proximal engagement feature 26 of an adjacent spacer 18 (see FIG. 5B).

The spacer 18 can include a biasing element 46 (e.g., a spring) disposed radially between the pin 42 and the body portion 52 (see FIG. 9B). The biasing element 46 can be positioned in the distal portion 62 of the lumen. The biasing element 46 can bias the pin 42 in a proximal direction to facilitate release of the humeral implant 2 from the locked configuration. As the locking element 38 is moved in a proximal direction, the biasing element 46 can facilitate movement of the pin 42 in a proximal direction to transition the implant 2 from the locked configuration (see FIG. 5B) to the unlocked configuration (see FIG. 5A).

The spacer 18 can include a feature to limit distal movement of the pin 42 and/or spring 46. For example, the spacer 18 can include a stopper 48. The stopper 48 can be annular and include an opening through which at least a portion of the pin 42 can extend (see FIG. 3). The stopper 48 can be positioned in a distal portion of the spacer 18, e.g., in the lumen 56 of the body portion 52 (see FIG. 9B) or at a distal end of the lumen 56. The stopper 48 can be secured to the body portion 52 (e.g., welded, adhered, press-fit, or otherwise). However, in other configurations, the lumen 56 can be shaped to limit both proximal and distal movement of the pin 42, a stopper 48 can limit both proximal and distal movement of the pin 42, or a stopper 48 can limit proximal movement of the pin 42 and a shoulder 54 can limit distal movement of the pin 42.

As shown in FIG. 9A, the spacer 18 can include at least one opening 43 along a lateral wall of the spacer 18. The one or more openings 43 provide access to flush out fluid or debris that may be in the spacer 18.

Figure 10:
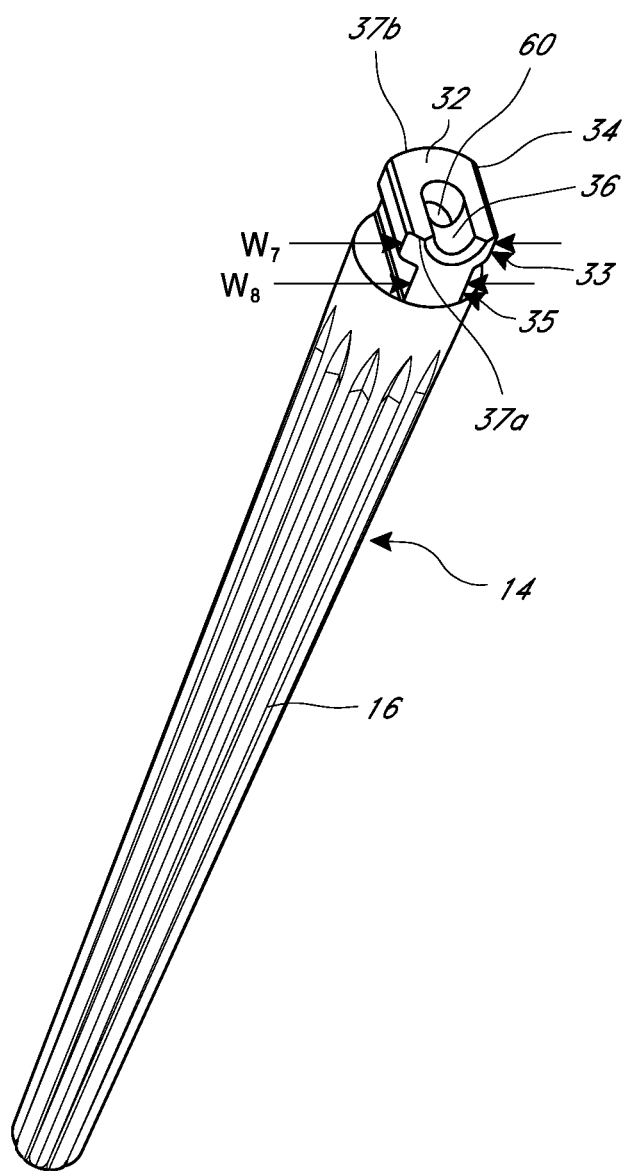
FIG. 10 illustrates a perspective view of a stem portion.

FIG. 10 illustrates the stem portion 14. The stem portion 14 can include an elongate body portion 16 and a stem engagement feature 34. The stem engagement feature 34 can be a T-shaped protrusion. The T-shaped protrusion can include a first portion 33 and a second portion 35. A width $w_7$ of the first portion 33 can be greater than a width $w_8$ of the second portion 35. The first portion 33 can form an end of the stem engagement feature 34. In certain embodiments, the stem may not be straight, but rather, curved along the longitudinal axis "L."

Figure 11:
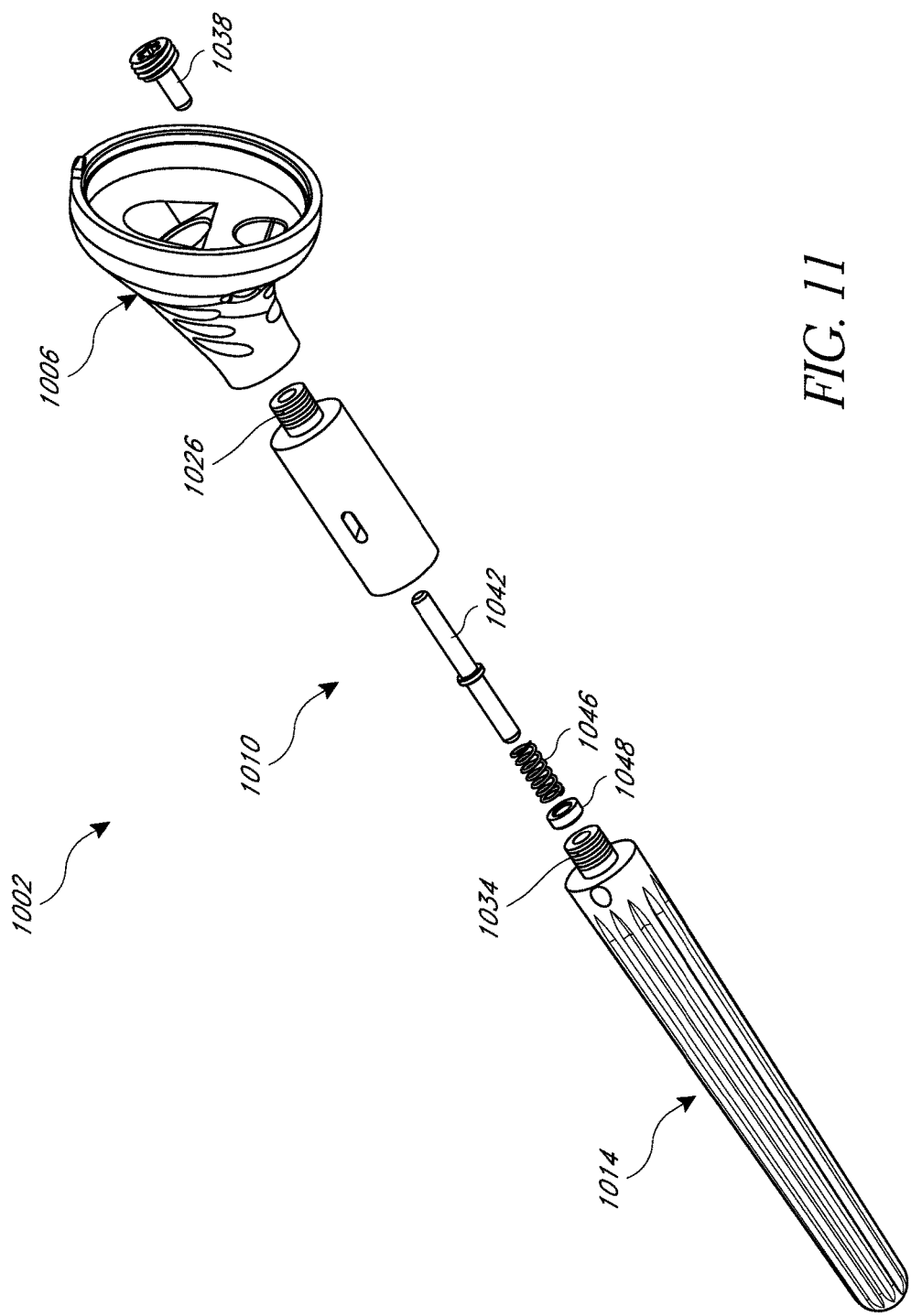
FIG. 11 illustrates an exploded view of an alternate embodiment of a humeral implant.

With reference to FIG. 11, another illustrative embodiment of a humeral implant 1002 is shown. The humeral implant 1002 resembles or is identical to the humeral implant 2 discussed above in many respects. Accordingly, numerals used to identify features of the humeral implant 2 are incremented by a factor of one thousand (1000) to identify like features of the humeral implant 1002. Any component or step disclosed in any embodiment in this specification can be used in other embodiments.

For a definitive humeral implant, it may be desirable to be able to secure together the metaphyseal portion 1006, the intermediate portion 1010, and the stem portion 1014 of the implant 1002. As shown in FIG. 11, the engagement features of the metaphyseal portion 1006, the intermediate portion 1010, and the stem portion 1014 can be threaded to threadably engage each other. The metaphysis portion 1006 can threadably engage a proximal engagement feature 1026 of the spacer 1018. The spacer 1018 can threadably engage a stem engagement feature 1034 of the stem portion 1014.

To further secure the metaphyseal portion 1006, the intermediate portion 1010, and the stem portion 1014 of the implant 1002 in a locked configuration, the implant 1002 can have a similar locking system to the humeral implant 2 in which distal movement of the locking member 1038 traverses a pin 1042 longitudinally to secure the implant 1002 in a locked configuration.

It should be noted that implants of the present disclosure may be provided with coatings on the surface thereof. More particularly, certain portions of the implants may include porous titanium coatings. Alternatively, or additionally biological coatings may be provided on the implants to promote bone growth. Such coatings are within the purview of those skilled in the art.

Humeral Implant with Multiple Spacers

Figure 2B:
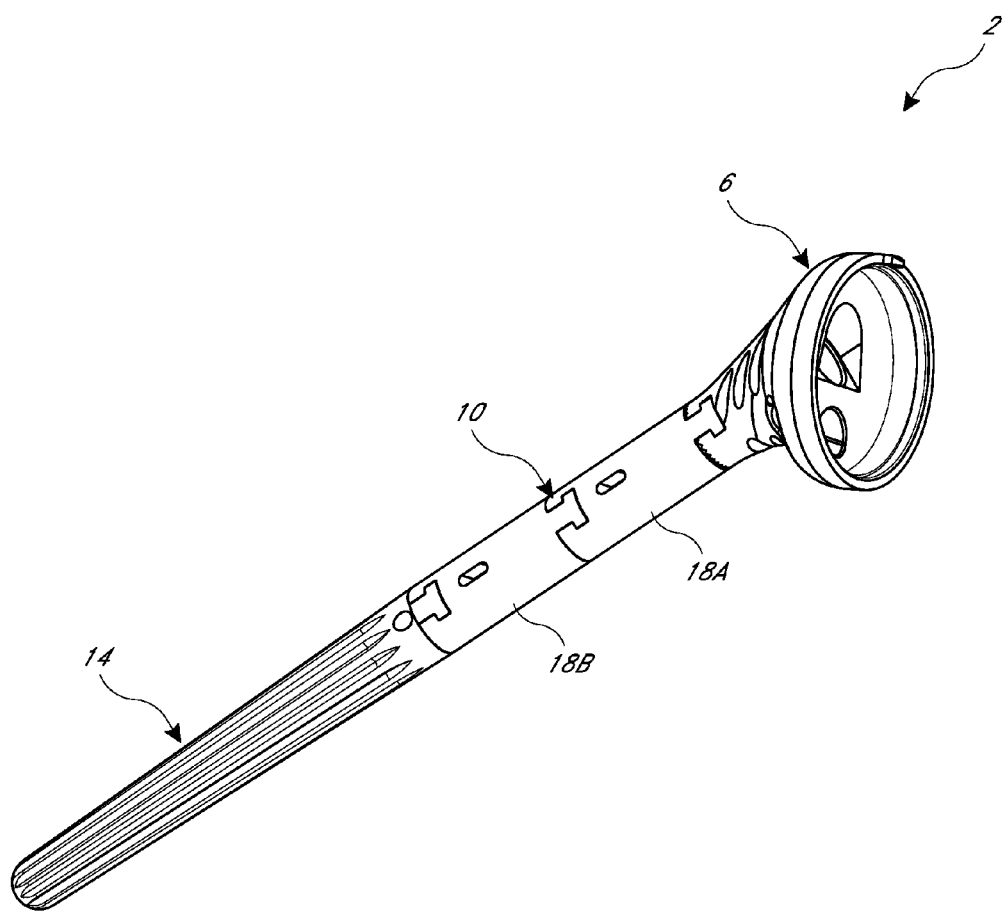
FIG. 2B illustrates a perspective view of an embodiment of a humeral implant including multiple spacers.

As shown in FIG. 2B, the intermediate portion 10 can include a plurality of spacers 18a, 18b (e.g., two, three, four, or more) to extend a length of the implant 2. To assemble an intermediate portion 10 with multiple spacers 18a, 18b a proximal engagement feature of a first spacer 18a can be configured to engage a distal engagement feature of a second, adjacent spacer, and so forth. For example, a proximal engagement feature of the first spacer 18a can be configured to engage the metaphyseal engagement feature, and a distal engagement feature of the second spacer 18b can be configured to engage the stem engagement feature 34. The distal engagement feature of the first spacer 18a can be configured to engage the proximal engagement feature of the second spacer 18b by sliding the second spacer 18b in a transverse direction relative to a longitudinal axis of the first spacer 18a. When the intermediate portion 10 is assembled, the lumens of the spacers form a single lumen extending longitudinally through the intermediate portion 10.

In some configurations, the spacers 18a, 18b can be configured to engage each other unilaterally (e.g., a first component can only engage a corresponding second component when the second component is in a single orientation/configuration or when the second component is introduced from a particular side). As discussed above, the orientation of engagement between adjacent portions may be limited by structures in the engagement features. For example, the proximal engagement features may include structures (e.g., grooves, channels, recesses, or otherwise) that limit the orientation in which the proximal engagement features can be introduced into corresponding engagement features. Limiting the orientation of assembly may be desirable to ensure each spacer is properly oriented.

Although not shown, if the intermediate portion 10 includes multiple spacers 18a, 18b, distal movement of the locking element 38 can translate the pin of each spacer 18a, 18b to secure the humeral implant 2 in the locked configuration. Distal movement of the locking element 38 can longitudinally translate each subsequent pin. The locking element 38 can translate the first pin of the first spacer 18a distally into a lumen of a second, adjacent spacer 18b. Distal movement of the first pin can translate a second pin in the second spacer, and so forth, until at least a distal portion of the pin of the distal-most spacer is positioned in the recess 60 of the stem portion 14. In the locked configuration, a distal end of the first pin contacts a proximal end of the second pin, and so forth such that the locking element 38 and the pins 42 form a continuous rod extending through the implant 2.

The spacers 18 may be offered in different lengths. By offering a range of standard spacer lengths surgeons can customize overall assembly length. This can reduce the number of trials required. For illustration purposes only, a set of three trials having 1 cm, 2 cm, and 3 cm lengths can be used to trial the following lengths: 1 cm, 2 cm, 3 cm, 4 cm, 5 cm, 6 cm. In this example, three modular trials can be used to model the same sizes as six monolithic trials. Using this reasoning, fewer expensive trial stems and fewer expensive trial metaphyses need be supplied provided a sufficient number of less expensive trial spacers are provided in a trial kit.

Method of Use

A trial humeral implant can include any combination of features described in connection with the humeral implants 2, 1002. In general, a metaphyseal portion 6,150, 1006, an intermediate portion 10,1010, and a stem portion 14,1014 can be assembled together and then locked together using the locking assembly described herein. Although the method below is described in connection with the reversed metaphyseal portion 6, the same method can be utilized for the anatomic metaphyseal portion 150.

The metaphyseal portion 6, the intermediate portion 10, and the stem portion 14 can be assembled together by sliding each portion in a transverse direction relative to a longitudinal axis of an adjacent portion. For example, the metaphyseal portion 6 and the intermediate portion 10 can be assembled by sliding the intermediate portion 10 in a transverse direction relative to a longitudinal axis of the metaphyseal portion 6 until the metaphyseal engagement feature 22 engages a proximal engagement feature 26 of the intermediate portion 10. The intermediate portion 10 and the stem portion 14 can be assembled by sliding the stem portion 14 in a transverse direction relative to a longitudinal axis of the intermediate portion 10 until a distal engagement feature 30 of the intermediate portion 10 engages a stem engagement feature 34. If the intermediate portion 10 includes multiple spacers 18, the intermediate portion 10 can be assembled by sliding each spacer in a transverse direction relative to a longitudinal axis of an adjacent spacer and into engagement with the adjacent spacer, until a proximal engagement feature of a first spacer engages a distal engagement feature of a second spacer.

After the trial humeral implant 2 has been assembled, the humeral implant 2 can be transitioned from an unlocked configuration (see FIG. 5A) to a locked configuration (see FIG. 5B). Distal movement of the locking element 38 can translate the pin 42 of each spacer 38 in a longitudinal direction until the humeral implant 2 is in the locked configuration. As the locking element 38 and the pin(s) 42 move distally, the locking element 38 is introduced into the spacer 18 such that the locking element 38 traverses the metaphyseal portion 6 and the intermediate portion 10, and the distal-most pin is introduced into the recess 60 of the stem portion such that the distal-most pin 42 traverses the stem portion 14 and the intermediate portion 10.

The locking element 38 can be driven by pushing, rotating, or otherwise moving the locking element 38 distally. As shown in FIGS. 5A and 5B, the locking element 38 can threadably engage the metaphyseal portion 6 (e.g., via right-handed or left-handed threads or other configurations). The locking assembly can be configured such that a single rotation (e.g., 360 degrees) of the locking element 38 transitions the humeral implant 2 between the unlocked configuration and the locked configuration. Although, the humeral implant 2 can be configured such that multiple rotations (e.g., two, three, or four) of the locking element 38 transition the humeral implant between the unlocked configuration and the locked configuration.

The assembled trial humeral implant 2 can be impacted into a resected humerus, leaving a portion of the metaphyseal portion 6 exterior to the bone (see FIG. 1). After determining the appropriate size of the articular component, the entire trial implant 2 can be removed using an extractor.

Based on the position of the assembled trial as impacted into the humerus, the dimensions of the definitive humeral implant can be selected. The definitive humeral implant can include any of the features of the humeral implant 2, 1002. If the definitive humeral implant includes slots and protrusions, the definitive humeral implant can be assembled as described above in connection with the trial humeral implant 2. If the definitive implant includes the connection features of the humeral implant 1002, the metaphyseal portion 1006, the intermediate portion 1010, and the stem portion 1014 can be screwed together. In another embodiment, the definitive humeral implant may be a monolithic structure instead of an assembly of components. Afterward, the humeral implant 1002 can be locked into a locked configuration by using the method described above in connection with the trial implant. Then, the definitive humeral implant can be implanted in the bone.

Over time, it may become necessary to perform a revision procedure to convert an anatomic metaphyseal portion 150 to a reversed metaphyseal portion 6. In those cases, it may be possible to remove only the anatomic metaphyseal portion 150 and leave the humeral stem in the bone. The reversed metaphyseal portion 6 can be trialed without engaging the metaphyseal engagement feature 22 with the implanted stem. The teeth on the distal surface 110 of the metaphyseal portion 6 can interface with the implanted stem to provide stability, while the trial metaphyseal portion 6 is locked together with the implanted stem. After determining the appropriate size for the metaphyseal portion, the definitive metaphyseal portion can be joined with the implanted stem.

Although certain embodiments have been described herein for a trial humeral implant, any of the components described herein can be used for a definitive humeral implant, or other trial or definitive implants for other anatomies such as femoral replacements or knee replacements.

Terminology

Certain embodiments have been described herein with a single spacer. However, any number of spacers can be used to form the humeral implant (e.g., two, three, four, or more). Further, the spacers in the humeral implant do not need to be identical. For example, the spacers can have different engagement features (e.g., threadable engagements, slidable engagements, etc.). As another example, the spacer may not include one or more of the spring, the stopper, and the flange portion of the pin.

Certain methods are described as sliding a first component relative to a second component. However, it should be understood that it is possible to slide the second component relative to the first component. For example, "sliding the intermediate portion in a transverse direction relative to a longitudinal axis of the metaphyseal portion" can also include "sliding the metaphyseal portion in a transverse direction relative to a longitudinal axis of the intermediate portion."

"Implant" is a broad term and is to be given its ordinary and customary meaning to a person of ordinary skill in the art and includes, without limitation, temporary implants (e.g., for trialing) or permanent implants (also referred to herein as definitive implants) for any anatomy, including, but not limited to, shoulder replacements, knew replacements, femoral replacements, and hip replacements.

As used herein, the term "metaphyseal portion" refers to either a reverse metaphyseal portion or an anatomic metaphyseal portion unless otherwise specified.

As used herein, the relative terms "proximal" and "distal" shall be defined from the perspective of the humeral component. Thus, proximal refers to the direction of the metaphyseal portion and distal refers to the direction of the stem portion.

For expository purposes, the term "transverse" as used herein is defined as a direction generally perpendicular to the longitudinal axis of the assembly, unless otherwise specified.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

The terms "approximately," "about," "generally," and "substantially" as used herein represent an amount close to the stated amount that still performs a desired function or achieves a desired result. For example, the terms "approximately," "about," "generally," and "substantially" may refer to an amount that is within less than 10% of the stated amount, as the context may dictate.

The ranges disclosed herein also encompass any and all overlap, sub-ranges, and combinations thereof. Language such as "up to," "at least," "greater than," "less than," "between" and the like includes the number recited. Numbers preceded by a term such as "about" or "approximately" include the recited numbers. For example, "about four" includes "four"

Any methods disclosed herein need not be performed in the order recited. The methods disclosed herein include certain actions taken by a practitioner; however, they can also include any third-party instruction of those actions, either expressly or by implication. For example, actions such as "distally moving a locking element" include "instructing distal movement of the locking element."

Although certain embodiments and examples have been described herein, it will be understood by those skilled in the art that many aspects of the humeral assemblies shown and described in the present disclosure may be differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, the scope of any and all embodiments having equivalent elements, modifications, omissions, combinations (e.g., of aspects across various embodiments), adaptations and/or alterations as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

Example Embodiments

The following example embodiments identify some possible permutations of combinations of features disclosed herein, although other permutations of combinations of features are also possible.

1. A humeral implant trial assembly comprising:
   a stem portion comprising a stem engagement feature;
   a metaphyseal portion comprising a metaphyseal engagement feature and a lumen extending longitudinally therethrough;
   a locking element positioned in the metaphyseal lumen of the metaphyseal portion; and
   an intermediate portion comprising at least one spacer, each spacer comprising:
     a proximal engagement feature;
     a distal engagement feature;
     a lumen extending longitudinally through said spacer, the lumen configured to be longitudinally aligned with the metaphyseal lumen when the trial assembly is in a locked configuration; and
     a pin slidable within the lumen of said spacer;
   wherein distal movement of the locking element translates the pin of each spacer to secure the metaphyseal portion, the intermediate portion, and the stem portion in the locked configuration.

2. The trial assembly of Embodiment 1, wherein each of the proximal engagement feature and the distal engagement feature is a T-shaped slot or a T-shaped protrusion.

3. The trial assembly of Embodiment 1 or 2, wherein the intermediate portion is configured to engage the metaphyseal engagement feature and/or the stem engagement feature by sliding the intermediate portion transverse to a longitudinal axis of the intermediate portion and into engagement with the metaphyseal engagement feature and/or the stem engagement feature.

4. The trial assembly of Embodiment 3, wherein the intermediate portion is configured to unilaterally engage the metaphyseal engagement feature and/or the stem engagement feature only by sliding the intermediate portion in a single direction transverse to a longitudinal axis of the intermediate portion.

5. The trial assembly of any one of the preceding Embodiments, wherein at least a portion of the lumen in the metaphyseal portion is threaded.

6. The trial assembly of any one of the preceding Embodiments, wherein the pin further comprises a flange portion, the flange portion configured to limit proximal and/or distal movement of the pin.

7. The trial assembly of any one of the preceding Embodiments, each spacer further comprises a stopper in the lumen of said spacer, the stopper configured to limit distal movement of the pin.

8. The trial assembly of any one of the preceding Embodiments, further comprising a spring positioned in the lumen of each spacer.

9. The trial assembly of Embodiment 8, wherein the spring is configured to bias the pin in a proximal direction.

10. The trial assembly of any one of the preceding Embodiments, wherein the stem portion further comprises a recess configured to receive the pin of one of said at least one spacer, the stem portion further comprising a channel extending from an outer surface of the stem portion to a distal end of the recess, the channel configured to receive an elongate structure to move the pin proximally and release the trial assembly from the locked configuration.

11. The trial assembly of any one of the preceding Embodiments, wherein the intermediate portion comprises a plurality of spacers.

12. The trial assembly of Embodiment 11, wherein each spacer is configured to engage an adjacent spacer by sliding said spacer transverse to a longitudinal axis of said spacer and into engagement with the adjacent spacer.

13. A spacer for use in a medical implant, the spacer comprising:
   a body portion, the body portion comprising a first engagement feature and a second engagement feature, each of the first engagement feature and the second engagement feature configured to engage other components of the medical implant;
   a lumen extending longitudinally through the body portion;
   a pin slidable through the lumen of the body portion, at least a distal portion of the pin comprising a smooth outer surface, the pin comprising a flange portion configured to limit proximal and/or distal movement of the pin; and
   a spring positioned radially between the pin and the body portion.

14. The spacer of Embodiment 13, wherein the medical implant is selected from the group consisting of a humeral implant and a femoral implant.

15. The spacer of Embodiment 13 or 14, wherein the medical implant is a trial implant.

16. A method of locking a trial humeral implant, the method comprising:
assembling a metaphyseal portion, an intermediate portion, and a stem portion, the assembling comprising:
sliding the intermediate portion into engagement with metaphyseal portion;
sliding the stem portion into engagement with intermediate portion, the intermediate portion comprising at least one spacer, each spacer comprising:
a proximal engagement feature;
a distal engagement feature;
a lumen extending longitudinally through said spacer; and
a pin slidable within the lumen of said spacer;
locking the trial humeral implant by distally moving a locking element disposed in the metaphyseal portion to translate the pin of each spacer to secure the metaphyseal portion, the intermediate portion, and the stem portion into a locked configuration; and
implanting the humeral implant in the locked configuration.

17. The method of Embodiment 16, wherein the intermediate portion comprises a plurality of spacers.

18. The method of Embodiment 27, further comprising assembling the intermediate portion by sliding each spacer transverse to a longitudinal axis of an adjacent spacer and into engagement with the adjacent spacer.

19. The method of any one of Embodiments 16 to 18, further comprising moving the locking element in a proximal direction to release the humeral implant from the locked configuration.

The following is claimed:

1. A humeral implant trial assembly comprising:
a stem portion comprising a stem engagement feature;
a metaphyseal portion comprising a metaphyseal engagement feature and a lumen extending longitudinally therethrough;
a locking element positioned in the metaphyseal lumen of the metaphyseal portion; and
an intermediate portion comprising at least one spacer, each spacer comprising:
a proximal engagement feature;
a distal engagement feature;
a lumen extending longitudinally through said spacer, the lumen configured to be longitudinally aligned with the metaphyseal lumen when the trial assembly is in a locked configuration; and
a pin slidable within the lumen of said spacer;
wherein distal movement of the locking element translates the pin of each spacer to secure the metaphyseal portion, the intermediate portion, and the stem portion in the locked configuration.

2. The trial assembly of claim 1, wherein each of the proximal engagement feature and the distal engagement feature is a T-shaped slot or a T-shaped protrusion.

3. The trial assembly of claim 1, wherein the intermediate portion is configured to engage the metaphyseal engagement feature and/or the stem engagement feature by sliding the intermediate portion transverse to a longitudinal axis of the intermediate portion and into engagement with the metaphyseal engagement feature and/or the stem engagement feature.

4. The trial assembly of claim 3, wherein the intermediate portion is configured to unilaterally engage the metaphyseal engagement feature and/or the stem engagement feature by sliding the intermediate portion in a single direction transverse to a longitudinal axis of the intermediate portion.

5. The trial assembly of claim 1, wherein at least a portion of the lumen in the metaphyseal portion is threaded.

6. The trial assembly of claim 1, wherein the pin further comprises a flange portion, the flange portion configured to limit proximal and/or distal movement of the pin.

7. The trial assembly of claim 1, wherein each spacer further comprises a stopper in the lumen of said spacer, the stopper configured to limit distal movement of the pin.

8. The trial assembly of claim 1, further comprising a spring positioned in the lumen of each spacer.

9. The trial assembly of claim 8, wherein the spring is configured to bias the pin in a proximal direction.

10. The trial assembly of claim 1, wherein the stem portion further comprises a recess configured to receive the pin of one of said at least one spacer, the stem portion further comprising a channel extending from an outer surface of the stem portion to a distal end of the recess, the channel configured to receive an elongate structure to move the pin proximally and release the trial assembly from the locked configuration.

11. The trial assembly of claim 1, wherein the intermediate portion comprises a plurality of spacers.

12. The trial assembly of claim 11, wherein each spacer is configured to engage an adjacent spacer by sliding said spacer transverse to a longitudinal axis of said spacer and into engagement with the adjacent spacer.

13. A spacer for use in a medical implant, the spacer comprising:
a body portion, the body portion comprising a first engagement feature and a second engagement feature, each of the first engagement feature and the second engagement feature configured to engage other components of the medical implant;
a lumen extending longitudinally through the body portion;
a pin slidable through the lumen of the body portion, at least a distal portion of the pin comprising a smooth outer surface, the pin comprising a flange portion configured to limit proximal and/or distal movement of the pin; and
a spring positioned radially between the pin and the body portion
wherein the medical implant is a humeral implant.

14. A method of locking a trial humeral implant, the method comprising:
assembling a metaphyseal portion, an intermediate portion, and a stem portion, the assembling comprising:
sliding the intermediate portion into engagement with metaphyseal portion;
sliding the stem portion into engagement with intermediate portion, the intermediate portion comprising at least one spacer, each spacer comprising:
a proximal engagement feature;
a distal engagement feature;
a lumen extending longitudinally through said spacer; and
a pin slidable within the lumen of said spacer;
locking the trial humeral implant by distally moving a locking element disposed in the metaphyseal portion to translate the pin of each spacer to secure the metaphyseal portion, the intermediate portion, and the stem portion into a locked configuration; and implanting the humeral implant in the locked configuration.

15. The method of claim 14, wherein the intermediate portion comprises a plurality of spacers.

16. The method of claim 15, further comprising assembling the intermediate portion by sliding each spacer transverse to a longitudinal axis of an adjacent spacer and into engagement with the adjacent spacer.

17. The method of claim 14, further comprising moving the locking element in a proximal direction to release the humeral implant from the locked configuration.

18. A spacer for use in a medical implant, the spacer comprising:
- a body portion, the body portion comprising a first engagement feature and a second engagement feature, each of the first engagement feature and the second engagement feature configured to engage other components of the medical implant;
- a lumen extending longitudinally through the body portion;
- a pin slidable through the lumen of the body portion, at least a distal portion of the pin comprising a smooth outer surface, the pin comprising a flange portion configured to limit proximal and/or distal movement of the pin; and
- a spring positioned radially between the pin and the body portion,
- wherein the medical implant is a femoral implant.

* * * * *

UNITED STATES PATENT AND TRADEMARK OFFICE
CERTIFICATE OF CORRECTION

PATENT NO. : 9,597,203 B2
APPLICATION NO. : 14/668892
DATED : March 21, 2017
INVENTOR(S) : Bradley Grant Emerick, Brian C. Hodorek and Matthew Victor Kartholl It is certified that error appears in the above-identified patent and that said Letters Patent is hereby corrected as shown below:

In the Claims

At Column 18, Line 47, In Claim 13, after "portion" insert --,--.

Signed and Sealed this
Twentieth Day of March, 2018

Andrei Iancu
*Director of the United States Patent and Trademark Office*